US00PP31348P2

(12) United States Plant Patent
Oudolf

(10) Patent No.: US PP31,348 P2
(45) Date of Patent: Jan. 14, 2020

(54) ***LAVATERA* PLANT NAMED 'DUET'**

(50) Latin Name: *Lavatera hybrida*
Varietal Denomination: Duet

(71) Applicant: Petrus Hendricus Oudolf, Hummelo (NL)

(72) Inventor: Petrus Hendricus Oudolf, Hummelo (NL)

(73) Assignee: FUTURE PLANTS LICENTIE B.V., Lisserbroek (NL)

( * ) Notice: Subject to any disclaimer, the term of this patent is extended or adjusted under 35 U.S.C. 154(b) by 0 days.

(21) Appl. No.: 16/350,879

(22) Filed: Jan. 28, 2019

(51) Int. Cl.
*A01H 5/02* (2018.01)
*A01H 6/60* (2018.01)

(52) U.S. Cl.
USPC ..... Plt./226

(58) Field of Classification Search
USPC ..... Plt./226
CPC ..... A01H 5/02; A01H 6/60; A01H 6/00
See application file for complete search history.

*Primary Examiner* — June Hwu
(74) *Attorney, Agent, or Firm* — C. A. Whealy

(57) ABSTRACT

A new and distinct cultivar of *Lavatera* plant named 'Duet', characterized by its upright and somewhat outwardly spreading plant habit; vigorous growth habit; freely branching habit; freely flowering habit; large rotate flowers that are light red purple, lighter red purple or white in color; and good garden performance and winter hardiness.

2 Drawing Sheets

Botanical designation: *Lavatera hybrida.*
Cultivar denomination: 'DUET'.

BACKGROUND OF THE INVENTION

The present invention relates to a new and distinct cultivar of *Lavatera* plant, botanically known as *Lavatera hybrida*, commercially known as Rose Mallow, and hereinafter referred to by the name 'Duet'.

The new *Lavatera* plant is a product of a planned breeding program conducted by the Inventor in Hummelo, The Netherlands. The objective of the breeding program was to develop new *Lavatera* plants with unique flower coloration.

The new *Lavatera* plant originated from a cross-pollination in 2015 of *Lavatera hybrida* 'White Angel', not patented, as the female, or seed, parent with *Lavatera hybrida* 'Summer Kisses', not patented, as the male, or pollen, parent. The new *Lavatera* plant was discovered and selected by the Inventor in 2015 as a flowering plant within the progeny of the stated cross-pollination in a controlled environment in Hummelo, The Netherlands.

Asexual reproduction of the new *Lavatera* plant by softwood cuttings in a controlled greenhouse environment in Lisse, The Netherlands since 2017 has shown that the unique features of this new *Lavatera* plant are stable and reproduced true to type in successive generations of asexual reproduction.

SUMMARY OF THE INVENTION

Plants of the new *Lavatera* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duet'.

These characteristics in combination distinguish 'Duet' as a new and distinct *Lavatera* plant:

1. Upright and somewhat outwardly spreading plant habit.
2. Vigorous growth habit.
3. Freely branching habit.
4. Freely flowering habit.
5. Large rotate flowers that are light red purple, lighter red purple or white in color.
6. Good garden performance and winter hardiness.

Plants of the new *Lavatera* can be compared to plants of the female parent, 'White Angel'. Plants of the new *Lavatera* differ primarily from plants of 'White Angel' in flower color as plants of the new *Lavatera* are light red purple, lighter red purple or white in color whereas plants of 'White Angel' have white-colored flowers.

Plants of the new *Lavatera* can be compared to plants of the male parent, 'Summer Kisses'. Plants of the new *Lavatera* differ primarily from plants of 'Summer Kisses' in flower color as plants of the new *Lavatera* are light red purple, lighter red purple or white in color whereas plants of 'Summer Kisses' have pale pink-colored flowers.

Plants of the new *Lavatera* can be compared to plants of *Lavatera hybrida* 'Barnsley Baby', disclosed in U.S. Plant Pat. No. 14,163. Plants of the new *Lavatera* differ primarily from plants of the 'Barnsley Baby' in flower color as plants of the new *Lavatera* are light red purple, lighter red purple or white in color whereas plants of 'Barnsley Baby' have white-colored flowers with red purple-colored centers.

Plants of the new *Lavatera* can be also compared to plants of *Lavatera hybrida* 'Sweet Dreams', not patented. Plants of the new *Lavatera* differ primarily from plants of the 'Sweet Dreams' in flower color as plants of the new *Lavatera* are light red purple, lighter red purple or white in color whereas plants of 'Sweet Dreams' have pink-colored flowers.

BRIEF DESCRIPTION OF THE PHOTOGRAPHS

The accompanying colored photographs illustrate the overall appearance of the new *Lavatera* plant showing the colors as true as it is reasonably possible to obtain in colored reproductions of this type. Colors in the photographs may differ slightly from the color values cited in the detailed botanical description which accurately describe the colors of the new *Lavatera* plant.

The photograph on the first sheet is a side perspective view of a typical flowering plant of 'Duet' grown in a container.

The photograph on the second sheet is a close-up view of typical flowers of 'Duet' at different stages of development.

DETAILED BOTANICAL DESCRIPTION

The aforementioned photographs and following observations, measurements and values describe plants grown in 25-cm containers during the summer in an outdoor nursery in Lisserbroek, The Netherlands under cultural practices typical of commercial *Lavatera* production. During the production of the plants, day temperatures ranged from 20° C. to 35° C. and night temperatures ranged from ranged from 12° C. to 22° C. Plants were one year old when the photographs and description were taken. In the description, color references are made to The Royal Horticultural Society Colour Chart, 2015 Edition, except where general terms of ordinary dictionary significance are used.

Botanical classification: *Lavatera hybrida* 'Duet'.

Parentage:

*Female, or seed, parent.*—*Lavatera hybrida* 'White Angel', not patented.

*Male, or pollen, parent.*—*Lavatera hybrida* 'Summer Kisses', not patented.

Propagation:

*Type.*—By softwood cuttings.

*Time to initiate roots, summer.*—About three weeks at temperatures about 20° C.

*Time to initiate roots, winter.*—About four weeks at temperatures about 20° C.

*Time to produce a rooted young plant, summer.*—About six weeks at temperatures about 20° C.

*Root description.*—Medium in thickness; fleshy; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Perennial shrub; upright and somewhat outwardly spreading plant habit; broad inverted triangle in overall shape; vigorous growth habit and rapid growth rate.

*Branching habit.*—Freely branching habit with typically about nine primary branches each with about five secondary lateral branches developing per plant.

*Plant height.*—About 87 cm.

*Plant diameter* (*area of spread*).—About 77.5 cm.

Lateral branch description:

*Length, primary branches.*—About 44.7 cm.

*Diameter, primary branches.*—About 7 mm.

*Internode length.*—About 5.9 cm.

*Aspect.*—About 25° to 70° from vertical.

*Strength.*—Strong.

*Texture and luster.*—Densely pubescent; matte.

*Color, developing and developed.*—Close to 143C.

Leaf description:

*Arrangement.*—Alternate, simple.

*Length.*—About 6.8 cm.

*Width.*—About 6.3 cm.

*Shape.*—Ovate in overall outline; palmately lobed.

*Apex.*—Broadly acute.

*Base.*—Truncate to reniform.

*Margin.*—Crenate to serrate; shallowly palmately-lobed with divergent sinuses.

*Texture and luster, upper and lower surfaces.*—Densely pubescent; slightly rugose; matte.

*Venation pattern.*—Palmate.

*Color.*—Developing leaves, upper surface: Close to 137B. Developing leaves, lower surface: Close to 137D. Fully expanded leaves, upper surface: Close to NN137B; venation, close to 144B. Fully expanded leaves, lower surface: Close to 147B; venation, close to 144C.

*Petioles.*—Length: About 6.1 cm. Diameter: About 2.5 mm. Strength: Strong. Texture and luster, upper and lower surfaces: Densely pubescent; matte. Color, upper surface: Close to 147B. Color, lower surface: Close to 143B.

*Stipules.*—Quantity and arrangement: Two, opposite, at the petiole attachment to the lateral branch. Length: About 1.2 cm. Width: About 3 mm. Shape: Lanceolate. Texture and luster, upper and lower surfaces: Moderately pubescent; matte. Color, upper and lower surfaces: Close to 137C.

Flower description:

*Flower appearance and arrangement.*—Large rotate flowers; flowers, arranged in terminal racemes or axillary; freely flowering habit with usually about 16 flowers developing per inflorescence and about 370 flowers developing per plant during the flowering season; flowers face mostly upright to slightly outwardly.

*Natural flowering season.*—Plants typically flower during the summer in The Netherlands; plants begin flowering about ten weeks after planting.

*Flower longevity.*—Flowers last about ten days on the plant; flowers not persistent.

*Fragrance.*—None detected.

*Inflorescence length.*—About 39.7 cm.

*Inflorescence diameter.*—About 8.8 cm.

*Flower diameter.*—About 8.1 cm.

*Flower length* (*height*).—About 2 cm.

*Flower buds.*—Length: About 1.3 cm. Diameter: About 8 mm. Shape: Ovoid. Texture and luster: Densely pubescent; matte. Color: Close to 145B; longitudinal ribs, close to 147C to 147D.

*Petals.*—Arrangement and quantity: Single whorl of five petals; petals separate. Length: About 4 cm. Width: About 2.4 cm. Shape: Sagittate. Apex: Deeply emarginate to cleft. Base: Cuneate. Margin: Entire. Texture and luster, upper surface: Smooth and mostly glabrous; at the base and basal margins, moderately pubescent; slightly glossy. Texture and luster, lower surface: Smooth and mostly glabrous; at the base and basal margins, moderately pubescent; moderately glossy. Color, light red purple-colored flowers: When opening, upper surface: Close to between 73B and 73C; towards the base, close to 61D. When opening, lower surface: Close to 62B; towards the base, close to 62A. Fully opened, upper surface: Close to between 73B and 75B; towards the base, close to 68B; venation, close to 68B; colors do not fade with development. Fully opened, lower surface: Close to 73C; towards the base, close to 68B to 68C; venation, close to 68B; colors do not fade with development. Color, lighter red purple-colored flowers: When opening, upper surface: Close to 69D; towards the base, close to 70D. When opening, lower surface: Close to 69D; towards the base, close to 69A. Fully opened, upper surface: Close to 69D; towards the base, close to 70D; venation, close to 73C; colors do not fade with development. Fully opened, lower surface: Close to 69D; towards the base, close to 69A; venation, close to 73C; colors do not fade with development. Color, white-colored flowers: When opening, upper and lower surfaces: Close to NN155D; towards the base, close to 62D. Fully opened, upper and lower surfaces: Close to NN155D; venation, close to NN155D; colors do not change with development.

*Sepals*.—Arrangement and quantity: Five in a single whorl. Length: About 1.2 cm. Width: About 7 mm. Shape: Ovate. Apex: Apiculate. Base: Fused. Margin: Entire. Texture and luster, upper and lower surfaces: Moderately pubescent; matte. Color: When developing, upper and lower surfaces: Close to 145B. Fully developed, upper and lower surfaces: Close to 144A to 144B; towards the base, close to 145A; apex tinged with close to 177D.

*Floral bracts*.—Quantity and arrangement: About three in a single whorl subtending the calyx. Length: About 1.2 cm. Width: About 9 mm. Shape: Broadly oblong. Color, upper surface: Close to 138B. Color, lower surface: Close to 138B; towards the base, close to 145C.

*Peduncles*.—Length: About 35.9 cm. Diameter: About 3 mm. Aspect: Erect to about 30° from the stem axis. Strength: Strong, flexible. Texture and luster: Densely pubescent; matte. Color: Close to 137C.

*Pedicels*.—Length: About 3 cm. Diameter: About 1.5 mm. Aspect: About 20° from the peduncle axis. Strength: Strong, flexible. Texture and luster: Densely pubescent; matte. Color: Close to 138B.

*Reproductive organs*.—Androecium: Quantity of stamens per flower: About 60. Filament length: About 6 mm. Filament color: Light red purple-colored flowers: Close to 75C. Lighter red purple-colored flowers: Close to 69B. White-colored flowers: Close to 69C to 69D. Anther shape: Double oblong. Anther length: About 1 mm. Anther width: About 0.5 mm. Anther color: Close to 155A. Amount of pollen: Moderate. Pollen color: Close to 159D. Gynoecium: Quantity of pistils per flower: Observed only on light red purple-colored flowers, about nine. Pistil length: About 1.5 cm. Style length: About 1.1 cm. Style color: Close to 148D. Stigma diameter: About 2 mm. Stigma appearance: Three-parted, cleft. Stigma color: Close to 62C. Ovary color: Close to 145B.

*Seeds and fruits*.—To date, seed and fruit development have not been observed on plants of the new *Lavatera*.

Garden performance: Plants of the new *Lavatera* have been observed to have good garden performance and to tolerate rain, wind, drought, temperatures ranging from about −12 C. to about 40° C. and to be suitable for USDA Hardiness Zones 8 to 11.

Pathogen & pest resistance: To date, plants of the new *Lavatera* have not been shown to be resistant to pathogens and pests common to *Lavatera* plants.

It is claimed:

1. A new and distinct *Lavatera* plant named 'Duet' as illustrated and described.

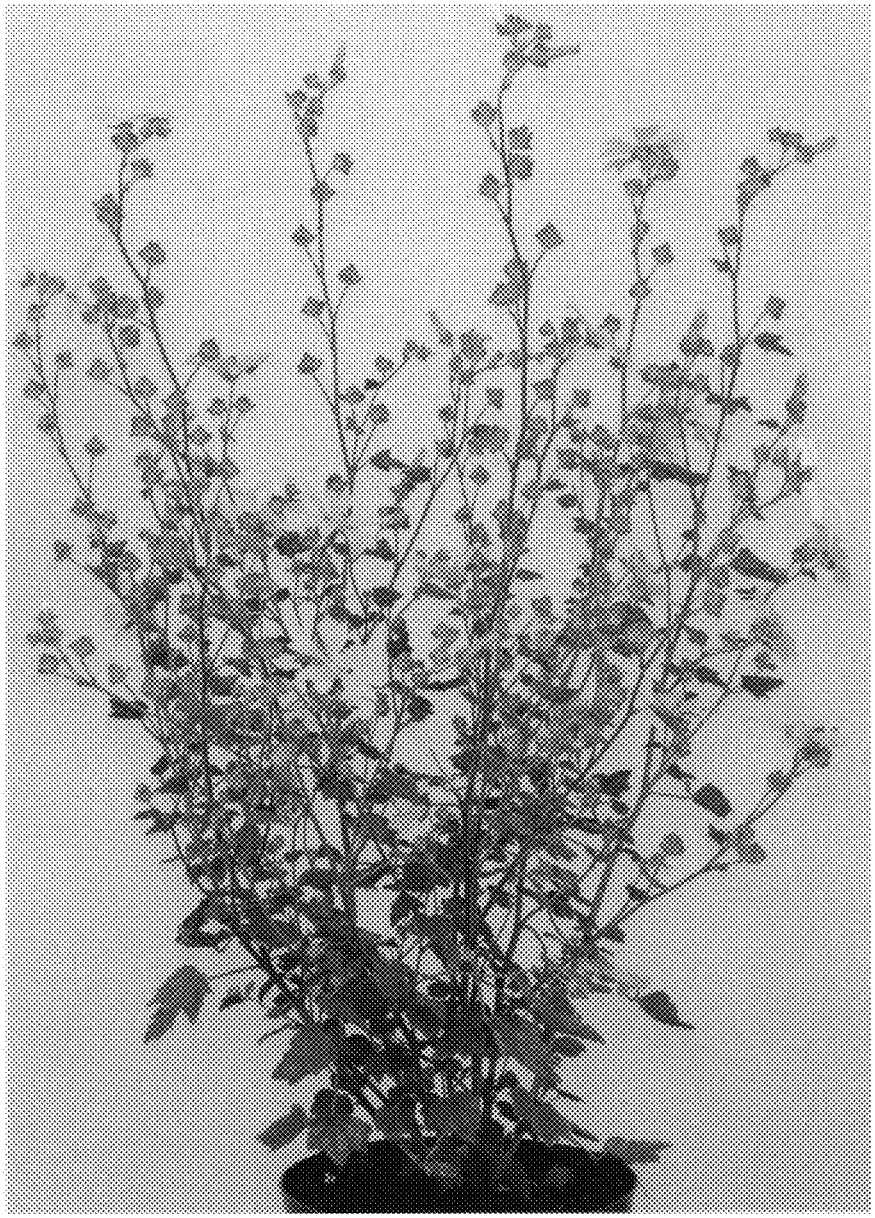

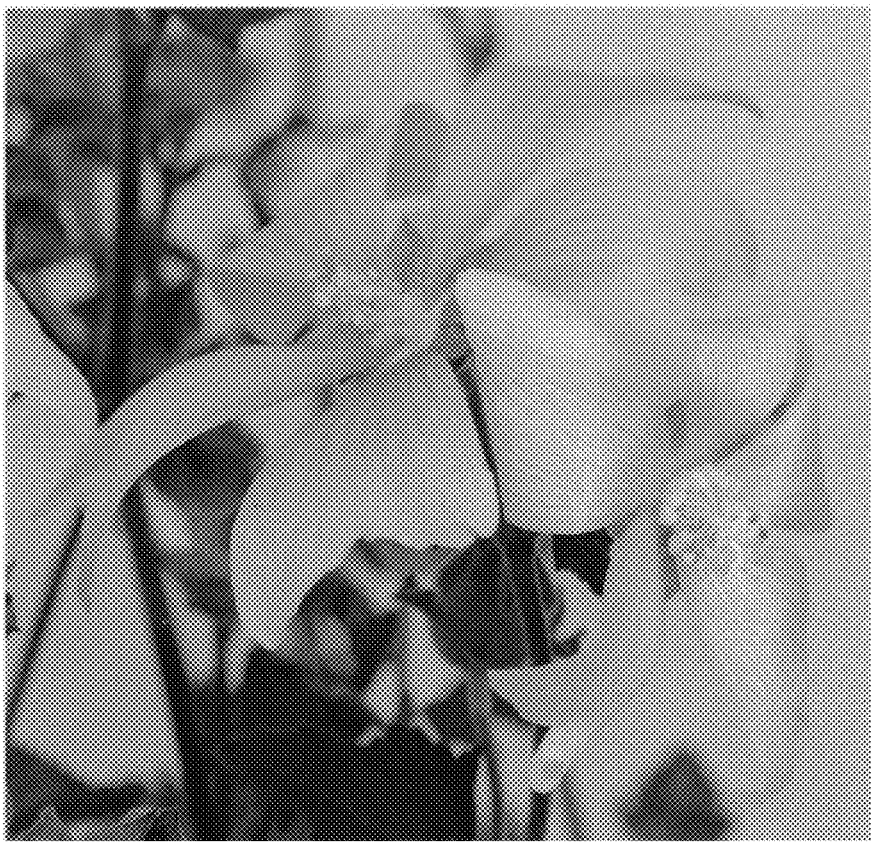

* * * * *